United States Patent [19]

Yamanaka

[11] 4,235,227

[45] Nov. 25, 1980

[54] ARTIFICIAL CORPUS CAVERNOSUM DEVICE

[76] Inventor: Hideo Yamanaka, No. 8-20, 4-chome, Meguro Hon-cho, Meguro-ku, Tokyo, Japan

[21] Appl. No.: 958,708

[22] Filed: Nov. 8, 1978

[51] Int. Cl.$^2$ ............................................. A61F 5/00
[52] U.S. Cl. ..................................................... 128/79
[58] Field of Search ................................. 128/79; 3/1

[56] References Cited

U.S. PATENT DOCUMENTS

| | | | |
|---|---|---|---|
| 3,853,122 | 12/1974 | Strauch | 128/79 |
| 3,954,102 | 5/1976 | Buuck | 128/79 |
| 4,009,711 | 3/1977 | Uson | 128/79 |

*Primary Examiner*—Lawrence W. Trapp
*Attorney, Agent, or Firm*—Jordan and Hamburg

[57] ABSTRACT

An artificial corpus cavernosum device which is designed to be implanted into the impaired penis of a patient for the remedy of his impotence and which comprises an at least one artificial corpus cavernosum penis of elongated tubular pouch made of an artificial thin membrane to be implanted into the penis and for selectively receiving and being filled with a fluid therein for erecting the penis, a container means made of an artificial thin membrane for storing said fluid under the normal condition when the penis is not inflated and hence not erected, the container means being implantable into the scrotum, a slenderized conduit means for connecting said at least one artificial corpus cavernosum penis to said container means in fluid communication with one another, and a check valve interposed in fluid communication with said container means and having a valve member provided with a through-hole(s) for allowing said fluid once forcibly delivered from said container means to pass to said artificial corpus cavernosum penis and to return to said container means again little by little through said through-hole(s).

10 Claims, 8 Drawing Figures

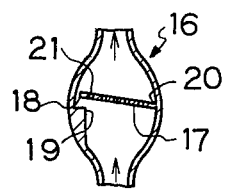
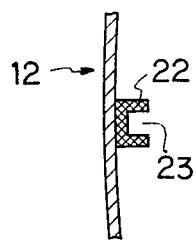
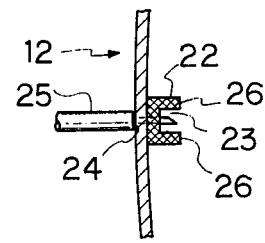
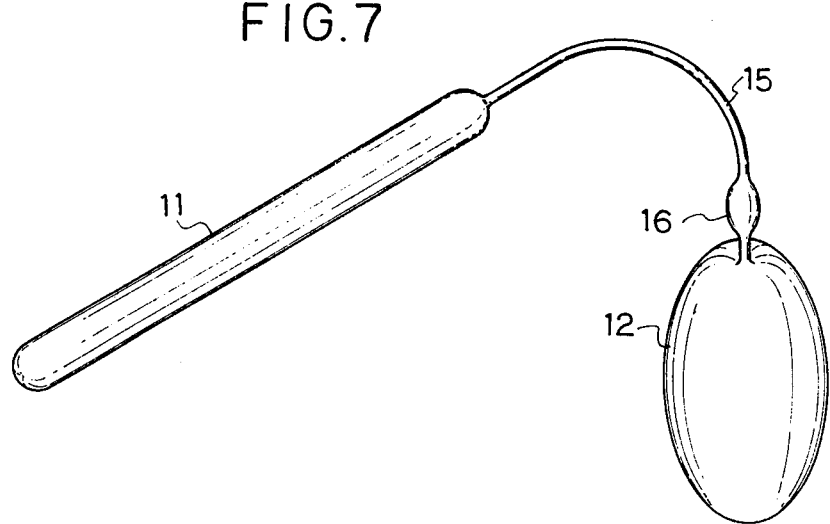

ARTIFICIAL CORPUS CAVERNOSUM DEVICE

BACKGROUND OF THE INVENTION

1. Field of the Invention

The present invention relates to an artificial corpus cavernosum device, and more particularly to an artificial corpus cavernosum device which is designed to be implanted into the penis of a patient for the management or remedy of impotence and which is discretionally adjustable to be brought to inflated condition.

The impotence may be caused by any of the organic damages such as congenital penile defect, tumor and the bending of the penis caused by elephantiasis or the like, the organic damages of the nervous systems such as the trauma of the spiral cord affected by exopathies, the diseases of endocrine origins such as the malformations of testis, glandula thyreoides and pitutitary bodies and diabates, and those caused by some mental shocks. The impotences resulted from some causes or having advanced to serious affection levels can not be cured without surgical therapy. In particular, there are not a little patients who can not perform the normal sexual lives irrespective of their holding of the normal semination functions and who thus are lack of the abilities to get children, which compel themselves to be separated from their wives. The present invention has been made to solve this serious impotence problem.

2. Prior Art

There has been known a prior art artificial device used for the remedy of impotence by a surgical operation, which device is designed to be implanted into the penis of a patient and comprises a solid bar of silicone resin. This known device is commonly called "silicone penile implant". In surgical remedy operation, one silicone penile implant may be implanted in-between the septum of the patient's corpus spongiosa penis, or alternatively two such silicone penile implants are implanted respectively into the left and right corpus spongiosa penis when his corpus spongiosa penis are diagnosed as entirely impossible to become turgid or inflated by the blood. No matter whether one or two silicone penile implants made of a solid silicone bar would be implanted or inserted into the patient's penis, such means is disadvantageous in that a silicone penile implant of the dimensions sufficiently large enough to hold his penis in fully erected condition can not be implanted in order not to hinder him from doing his daily and ordinary actions such as walking. Hence, in most known cases, there are used, to implant into patients' penes, the silicone penile implants of the dimensions which serve to hold the penes in only half-erected conditions, in view of the fact that these known silicone penile implants are in fact soft but not elastically adjusted. However, since the penis of the patient is always held in half-erected conditions, it is continuously oppressed by his garment and occationally causing a troublesome disaster wherein it is stuck into the soft part at the lower part of the vesica urinalis adjacent thereto. For the reasons set forth above, this known device is not an advantageous one.

Another type known artificial device used for the remedy of impotence is composed of a soft spongy body and ribbons attached to the spongy body. Said spongy body is applied to the urethrae of a patient and said tapes are softly tied over the corpus spongiosa penis at the crus of the penis, whereby the blood in the corpus cavernosa filled therein is held in hyperemia or passive hyperemia condition. However, in this known prosthesis method, the urethrae is tied by the tape together with the corpus cavernosa to cause bad affection on the discharge of the urine. A further disadvantage of this known device is that the erection function thereof is poor and thus the perfect impotence can not be recovered to any appreciable extent.

In accordance with the present invention, the disadvantages of the prior art devices can be overcome, as will be apparent from the detailed description thereof set forth hereinafter.

OBJECTS AND SUMMARY OF THE INVENTION

A principal object of the present invention is to provide an artificial corpus cavernosum device which has the ability of perfectly erecting the penis of a patient during sexual intercourse and may be controlled in a simple fashion for bringing the same in contraction condition during the ordinary life time other than sexual intercourse.

Another object of the present invention is to provide such artificial corpus cavernosum device which is safety and perfectly harmless to the human body.

A further object of the present invention is to provide a novel artificial corpus cavernosum device which is to be implanted into the patient's penis while retaining the device in uninflated condition and which device can be adjusted to have any desired inflation volume for erecting the penis at the most appropriate angle and volume in a very simple manual operation after being implanted.

Yet a further object of the invention is to provide an artificial corpus cavernosum device which may be simply repaired after the implanation operation.

According to the present invention, there is provided an artificial corpus cavernosum device which comprises an at least one artificial corpus cavernosum penis of elongated tubular pouch made of an artificial thin membrane to be implanted into the penis and for selectively receiving and being filled with a fluid therein for erecting the penis, a container means made of an artificial thin membrane for storing said fluid under the normal condition when the penis is not inflated and hence not erected, the container means being implantable into the scrotum, a slenderized conduit means for connecting said at least one artificial corpus cavernosum penis to said container means in fluid communication with one another, and a check valve interposed in fluid communication with said container means and having a valve member provided with a through-hole(s) for allowing said fluid once forcibly delivered from said container means to pass to said artificial corpus cavernosum penis and to return to said container means again little by little through said through-hole(s).

BRIEF DESCRIPTION OF THE DRAWINGS

The above and other objects and inventive features of the invention will be apparent from the following detailed description thereof when taken in conjugation with the accompanying drawings, in which:

FIG. 5 is a sectional view taken along line C—C in FIG. 1;

FIGS. 6a and 6b are views showing the sections along line D—D in FIG. 1, while in FIG. 6b an injection needle with a shoulder is shown as piercing through the specified portion of a fluid container of the artificial corpus cavernosum device of the invention; and FIG. 7 is a perspective view of another embodiment of the artificial corpus cavernosum device according to the invention.

DESCRIPTION OF THE PRESENTLY PREFERRED EMBODIMENTS

The presently preferred embodiments of the invention will now be described hereinbelow with reference to the appended drawings.

Figure 1:
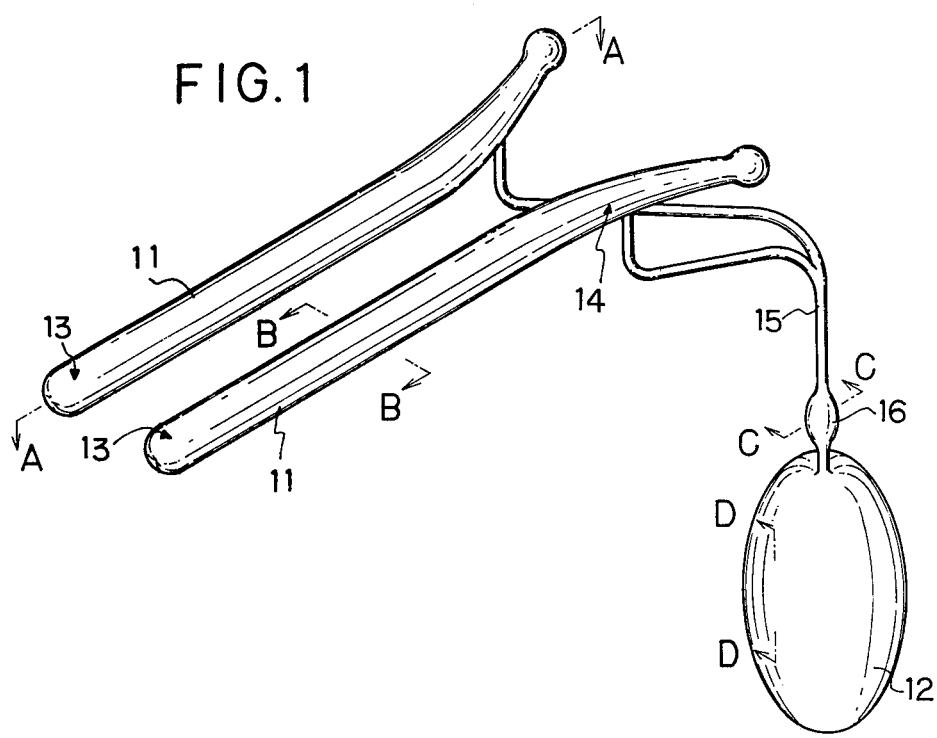
FIG. 1 is a perspective view of one embodiment of the artificial corpus cavernosum device according to the invention.

Referring to FIG. 1, a perspective view of an inflated artificial corpus cavernosum device 10 according to the invention is shown. In actual operation, when artificial corpus cavernos penis or elongated tubular pouches 11 as shown are inflated, a container means or tank 12 made of a thin membrane material becomes uninflated condition as will be described hereinafter and vice versa. Nevertheless, both members are shown as being inflated simultaneously for the clarification purpose. The artificial corpus cavernosa penis of this embodiment are made of elongated tubular pouches and correspond to the unimpaired corpus spongiosa penis, which can be filled with and hold a fluid therein. The fore-end portion 13 of the artificial corpus cavernosum penis 11 may be formed to have a diameter larger than that of the rear portion 14, or the artificial corpus cavernosum penis 11 may have a generally uniform diameter in its entirety. The embodiment shown in FIG. 1 has two artificial corpus cavernosa penis 11 and may be applied to a patient who is diagnosed to have the corpus spongiosa penis which can not become turgid to reach hypermia condition. The artificial corpus cavernosa penis 11 are inserted or implanted into the right and left corpus spongiosa penis of the patient, respectively. The length of each of the artificial corpus cavernosa penis 11 in the longitudinal direction is not limited, but is preferably such that the fore-end thereof extends slightly beyond the collum glandis and the rear end thereof extends adjacent to the rear end or base portion of the corpus spongiosum penis when implanted.

Figure 2:
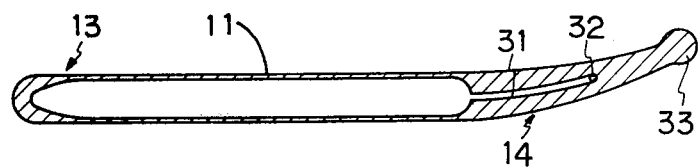
FIG. 2 is a top plan view showing a longitudinal section taken along line A—A in FIG. 1.

In FIG. 2 a top plan view showing a longitudinal section of the artificial corpus cavernosum penis taken along line A—A in FIG. 1 is shown. The rear portions 14 of the artificial corpus cavernosa penis 11, which correspond to those portions existing within the truncus when implanted into the right and left corpus spongiosa penis, respectively, are made solid. The solid rear portion 14 is provided with a passage 31 for fluid communication therethrough. A passage inlet 32 is connected in fluid flow communication with a slenderized tube 15. The rear end portion 33 is preferably shaped as round.

Since the rear or base portion 14 is solid, the artificial corpus cavernosum penis 11 is firmly implanted. The rear portion 14 existing within the truncus when implanted is susceptible to shocks due to motions of patient's feet. The rear portion 14 has, however, little danger of being damaged by such socks because of its solid structure so that the device of the invention functions without any trouble. Furthermore, the round rear end portion 33 prevents the corpus spongiosum penis from being damaged due to shocks carried by the artificial corpus cavernosum penis 11 during sexual intercourse.

Figure 3:
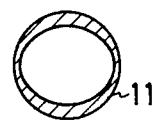
FIG. 3 is a sectional view of the device taken along line B—B in FIG. 1.
Figure 4:
FIG. 4 is a similar sectional view but showing uninflated condition of the device.

FIG. 3 shows a sectional view of one of the artificial corpus cavernosa penis 11 when taken along line A—A in FIG. 1. As shown, the wall thicknesses of the portions forming the longitudinally extending upper and lower sides of the pouch 11 are thicker than the wall thickness of the longitudinally extending side wall portions of said pouch in the implanted condition. Being formed as such and being implanted to such position, it may be naturally brought to the condition shown in FIG. 3 wherein it is folded along the thin membrane side walls which form the bending portions. As a result, the penis naturally hangs down, thus being very convenient for daily life. If the thin membrane thickness in the vicinity of the fore-end 13 is thicker (see FIG. 2), the artificial corpus cavernosa penis 11 are given proper hardness at its fore-end 13 when inflated.

A thin or slenderized tube or conduit means 15 is connected in fluid flow communication to the rear portion 14 of the pouch 11. For the operational convenience, it is preferred that the passage inlet 32 be on under side when implanted. The pouch 11 may or may not be formed integrally of the slenderized tube 5. In the embodiment shown in FIG. 1, the slenderized tubes connected to the right and left pouches 11 are conjoined together to form a unified thin tube the end of which is connected to a check valve 16. The length of the thin tube or tubes is such that the artificial container means or tank 12 is implanted at the upper and central portion of the scrotum when the pouches 11 are implanted into the corpus spongiosa penis.

FIG. 5 shows a section of the check valve 16 taken along line C—C in FIG. 1. The check valve 16 and the thin tube 15 may be formed as an integral body, but it is preferred to form them as separate and independent components and detachably attached with each other in order to make it easy to exchange the impaired check valve 16 if the latter is damaged or impaired or the function thereof is badly affected. The check valve shown in FIG. 5 comprises a valve member 17 with a fringe portion 18 abuttable on a shoulder 19 formed on the inner periphery of the wall of the housing of the check valve, the valve member 17 being pivotal about a support portion 20. The valve member 17 is provided with a plurality of through-holes 21. The fluid storage tank 12 of artificial thin membrane is compressed to allow the fluid contained therein to pass therefrom to push up the valve member 17 and to flow through the thin tube 15 into the pouches 11 to inflate the same. The fluid delivered into each artificial corpus cavernosum penis or pouch 11 can not be flown back in the reverse direction since the fringe portion 18 is engaged with and stopped by the shoulder 19 so that the fluid is not immediately returned to the fluid storage tank 12 and hence the artificial corpus cavernosa penis 11 are held at their inflated conditions. As the result, the penis is held at its erected condition. The fluid in the pouches 11 is returned little by little through the through-holes 21 into said fluid storage tank 12, and consequently the volume of the fluid contained in the pouches 11 is finally returned to said tank 12 after the lapse of a predetermined time period. As the result, the artificial corpus cavernosa penis 11 are restored to uninflated conditions and the penis hangs down into contraction state, accordingly.

FIG. 6a shows a section of the fluid storage tank 12 of an artificial thin membrane taken along line D—D in FIG. 1. The fluid storage tank 12 is implanted into the scrotum at the upper portion between the right and left testes. Since the derma of the scrotum is elastic or expandible, there is a sufficient space in which the fluid storage tank 12 is implanted. As is shown in FIG. 6a, the fluid storage tank 12 is provided with a fluid injection portion 22. This fluid injection portion 22 may be formed by thickening the specified portion of the thin membrane or alternatively may be formed from discrete components made by an independent step and made of another material, which is then attached to the specified portion of the membrane. Centrally thereof provided is a recess 23. It is preferred that the artificial corpus cavernosum device of the present invention is implanted by a surgical operation while any considerable amount of the fluid is contained therein and then the fluid is injected therein after the completion of the implantation. FIG. 6b shows the artificial corpus cavernosum device of the invention under the injection operation. An injection needle 25 provided with a shoulder 24 is mounted to an injector (not shown) and the needle 25 is pierced at the recessed portion 23 of the fluid injection portion 22. Since the shoulder 24 of the injection needle 25 is engaged with and stopped by the outside surface of the membrane constituting the fluid storage tank 12, thereby preventing the tip end of the needle 25 from extending beyond the edge 26 of the fluid injection portion 22, there is no fear for the injection needle 25 to pierce into and damage the membrane of the fluid storage tank 12 during the fluid injection operation. The fluid may be injected into the tank by the use of an injection needle piercing through the derma of the scrotum in a very simple manner, and the injected volume thereof may be properly adjusted or added at later time.

FIG. 7 shows another embodiment of the present invention, in which the similar members to those of the embodiment shown in FIG. 1 are designated by the same reference numerals. The artificial corpus cavernosum device according to this embodiment has only one artificial corpus cavernosum penis or elongated tubular pouch 11 and is used to remydy a patient whose right and left corpus spongiosa penis can be filled with blood to be inflated. By a surgical operation, this artificial corpus carvenosum penis 11 is inserted or implanted into the septum of the corpus cavernosa. The length in the longitudinal direction of the artificial corpus cavernosum penis 11 is such that the fore-end thereof extends slightly beyond the collum glandis and the rear end thereof terminates generally on the upper critical line along which both of the right and left corpus spongiosa penis includes the corpus cavernosui urethae. In this embodiment, there are no portions to be implanted within the truncus. Hence, the substantially entire length of the pouch 11 is hollow. Preferably, the tube 15 may be connected to the pouch 11 at its rear end. The other parts of this embodiment are similar to those of FIG. 1.

The artificial corpus cavernosum device according to the present invention may be made of any material which are harmless to the human bodies and with which the functions of the device of the invention may be exerted to a desired extent. An example of the preferable materials is a silicone resin. The fluids which may be used in the present invention include an isotonic sodium chloride solution, a silicone oil, oily materials such as minerial oils, glycerin and olive oil. The most preferred fluid is the isotonic sodium chloride solution because it causes utterly no harm if it should leak out of the device.

While the present invention has been described with reference to the specific embodiments of the invention, it is by no means intended to limit the scope of the invention but to include all modifications, deviations and changes without departing from the spirit of the invention.

What is claimed is:

1. An artificial corpus cavernosum device comprising:
   an at least one artificial corpus cavernosum penis of elongated tubular pouch made of an artificial thin membrane to be implanted into the penis and for selectively receiving and being filled with a fluid therein for erecting the penis;
   a container means made of an artificial thin membrane for storing said fluid under normal condition when the penis is not inflated and hence not erected, the container means being implantable into the scrotum;
   a slenderized conduit means for connecting said at least one artificial corpus cavernosum penis to said container means in fluid communication with one another; and
   a check valve interposed in fluid communication with said container means and having a valve member provided with a through-hole(s) for allowing said fluid once forcibly delivered from said container means to pass to said artificial corpus cavernosum penis and to return to said container means again little by little through said through-hole(s),
   said container means being provided with a thick-wall projection having at the center thereof a sunk recess, said projection being attached on the inner face of said container means, whereby the tip end of a needle of an injection tube may be pierced through said center of said thick-wall projection so that said tip end is within the sunk recess, thereby injecting said fluid into said container means without injuring the artificial membrane of said container means.

2. An artificial corpus cavernosum device according to claim 1, wherein the wall thickness of said membrane in the vicinity of the closed fore-end of said pouch and the wall thicknesses of the portions forming the longitudinal upper and lower sides of said pouch are thicker than the wall thickness of the longitudinal side wall portions of said pouch when said pouch is implanted into the penis.

3. An artificial corpus cavernosum device according to claim 1, wherein said container means is detachably connected.

4. An artificial corpus cavernosum device according to claim 1, wherein said check valve is detachably interposed between said conduit means and said container means.

5. An artificial corpus cavernosum device according to claim 1, wherein said fluid is a liquid selected from the group consisting of an isotonic sodium chloride solution, a silicone oil, glycerin and olive oil.

6. An artificial corpus cavernosum device according to claim 5, wherein said fluid is an isotonic sodium chloride solution.

7. An artificial corpus cavernosum device according to claim 1, wherein said two artificial corpus cavernosa penis are connected in fluid communication with each of the slenderized conduit means, the longitudinal lengths of the artificial corpus cavernosa penis are such that when each is implanted into the right and left corpus spongiosum penis the fore-end of the artificial corpus cavernosum penis extends slightly beyond the collum glandis and the rear end thereof extends adjacent to the rear end of the corpus songiosum penis, the rear portion of the artificial corpus cavernosum penis which corresponds to that portion existing within the truncus when implanted being made solid, said solid rear portion being provided with a fluid flow passage and the inlet of the passage being connected to said conduit means.

8. An artificial corpus cavernosum device according to claim 7, wherein said passage inlet is provided at the under side of the rear portion of said artificial corpus cavernosum penis when implanted.

9. An artificial corpus covernosum device according to claim 7 or 8, wherein the rear end of the artificial corpus cavernosum penis is round.

10. An artificial corpus cavernosum device according to claim 1, wherein said one artificial corpus cavernosum penis is connected in fluid communication with the slenderized conduit means, the longitudinal length of the artificial corpus cavernosum penis being such that when implanted into the septum of the corpus spongiosum penis the fore-end thereof extends slightly beyond the collum glandis and the rear end thereof terminates generally on the upper critical line along which the right and left corpus spongiosa penis includes the corpus cavernosui urethae, the artificial corpus cavernosum penis being hollow along the entire length thereof and connected to said conduit means at its rear portion.

* * * * *